US009084905B2

(12) United States Patent
Campbell

(10) Patent No.: US 9,084,905 B2
(45) Date of Patent: Jul. 21, 2015

(54) AIR FILTRATION APPARATUS AND METHOD

(76) Inventor: Cecil E. Campbell, San Pedro, CA (US)

( * ) Notice: Subject to any disclaimer, the term of this patent is extended or adjusted under 35 U.S.C. 154(b) by 1140 days.

(21) Appl. No.: 12/907,993

(22) Filed: Oct. 20, 2010

(65) Prior Publication Data

US 2011/0030691 A1 Feb. 10, 2011

Related U.S. Application Data

(62) Division of application No. 12/236,617, filed on Sep. 24, 2008, now abandoned.

(51) Int. Cl.
*A61M 11/00* (2006.01)
*A62B 7/12* (2006.01)
*A63B 71/00* (2006.01)

(52) U.S. Cl.
CPC .. *A62B 7/12* (2013.01); *A63B 71/00* (2013.01)

(58) Field of Classification Search
CPC ............ A61M 16/208; A61M 16/105; A62B 23/025; A62B 7/10; A62B 18/02; A62B 23/00
USPC ........................................ 128/205.29–206.19
See application file for complete search history.

(56) References Cited

U.S. PATENT DOCUMENTS

| | | | |
|---|---|---|---|
| 6,971,388 | B1 | 12/2005 | Michaels |
| 7,380,551 | B2 | 6/2008 | Alvey |
| 7,392,806 | B2 | 7/2008 | Yuen et al. |
| 7,406,966 | B2 | 8/2008 | Wondka |
| 2008/0168996 | A1 | 7/2008 | Willis |
| 2008/0190436 | A1 | 8/2008 | Jaffe et al. |

*Primary Examiner* — Steven Douglas`

(57) ABSTRACT

An air filtration apparatus is disclosed. During inhale response, user's breath opens a first air valve causing air flow through replaceable filter through a chamber to a mouth piece disposed in a user's mouth. During exhale response, user's breath closes first valve causing one or more exhaust valves to open. In one embodiment, inhale and exhale responses are displaced from one another to provide better isolation of replaceable filter.

12 Claims, 4 Drawing Sheets

AIR FILTRATION APPARATUS AND METHOD

PRIORITY APPLICATION

This application is a divisional application of and claims priority to U.S. utility patent application Ser. No. 12/236,617 filed on Sep. 24, 2008 now abandoned, entitled "AIR FILTRATION APPARATUS AND METHOD", and contents of which are incorporated by reference in their entirety in this application.

BACKGROUND OF THE INVENTION

1. Field of the Invention

The invention relates generally to the field of athletic and sports breathing gear and assemblies, and more specifically in one exemplary aspect to an air filtration mouth piece and apparatus to reduce dust, smoke, and allergen related illnesses.

2. Description of Related Technology

Air filtering and breathing assemblies are well known in the art. Such assemblies are utilized to prevent or reduce the opportunity of lung related illness when participating in activities in high smoke, high pollutant, and high allergen environments. Some related art patents discussed below (and incorporated by reference in their entirety) are representative art of these conventional assemblies. In one related art example, US 2008/0168996 published Jul. 17, 2008, by Willis et al. entitled "ANIMASKS KID'S DUST MASKS AKA CHILD FRIENDLY FILTER MASK" discloses a mask made of printed die-cut cotton fibers for versatile fund character designs, with OEM Adjusters and staples. In yet another related art example, US2008/0190436 entitled "NASAL AND ORAL PATIENT INTERFACE" by Jaffe et al. published Aug. 14, 2008, discloses a patient interface for communicating fluids to and/or from a patient nasal cavity and/or oral cavity.

In another related prior art, U.S. Pat. No. 7,406,966 entitled "METHOD AND DEVICE FOR NON-INVASIVE VENTILATION WITH NASAL INTERFACE" by Wondka issued Aug. 5, 2008, discloses a nose ventilation interface including a pair of tubes to deliver a ventilation gas. The tubes are attachable at a first end to a ventilation gas supply hose and engageable at a second end with a person's nostril. In yet another related art, U.S. Pat. No. 7,392,806 issued Jul. 1, 2008, entitled "ELECTRONIC HUMAN BREATH FILTRATION DEVICE" by Yuen et al. discloses a portable human body carrying electronic human filtration device that is an electronic nose mask. The device utilizes electronic ionization technique and electrostatic field to remove air borne particles, dust, pollen, contaminants, bacteria, viruses, toxic chemical, fume and tobacco smoke from human inhalation and exhalation breath. In another related prior art, U.S. Pat. No. 7,380,551 entitled "BREATHING APPARATUS" by Alvery that issued Jun. 3, 2008, discloses an SCBA system for providing bottled air to a user and a PAPR system for purifying ambient air for use by a user. In yet another related prior art, U.S. Pat. No. 6,971,388 entitled "INTERNAL NASAL DILATOR FILTER" by Michaels issued on Dec. 6, 2005, discloses a nasal filtration and internal nasal dilation system that operate synchronously to provide air filtration by retaining particle in a single piece foam nasal filter during inhalation through the nose.

In contrast to the above instances, air filtering apparatus may further be desired to achieve still wider variety of protection and/or air cleaning options and provide improved user comfort and wearing pleasure as well as provide various types of and configurations that are adjustable to fit a user without requiring complicated attachment/de-attachment hardware. In one instance, eliminate or reduce the need for professionals or buckles, bolts, or screws to secure an air filtration apparatus to your body. In yet another instance, an air filtration device may be needed that provides breathability and airflow at least in designated areas or expose a larger effective surface area so that a more consistent air flow may be realized a user. In another instance, a manufacturer or user may find it beneficial that a protective device have one or more removable and replaceable and washable components. Furthermore, a user may further desire the prospective device to be easily assembled or disassembled "on the fly" and easily installed or removed on a user's body in a minimal time. In addition, a user desires the protective device durable but also conformable to wear and to create minimal restriction in a user's movement or normal breathing pattern.

Thus, what is needed are improved protective apparatus and methodology that permits easy initial configuring and reconfiguring, i.e., provide adaptability, and upgrade capability so that the same unit be utilized (or added-on to) if new functionality (e.g., chest protection) is desired. Furthermore, such improved apparatus and methods would also ideally allow a person other than a professional or licensed personal to adjust or retrofit the air filtration device, and would further permit creation of user-customized air filtration configurations and customized fit and appearance of the air filtration device as well as new patterns requiring minimal efforts, e.g., minimal adjustment or removal and replacement or adaptation of existing components. Furthermore, the device should provide improved air flow so that condensation is prevented from building up in the air filtration device.

SUMMARY OF THE INVENTION

In one aspect of the present invention, an air filtration assembly is disclosed. The air filtration assembly includes a replaceable filter shaped to conform to a user's mouth piece area.

During inhale, a user's breath opens a first air valve causing air flow through the replaceable filter through a chamber to a mouth piece disposed in a user's mouth. In one embodiment, the first air value opens, in one instance, parallel to air flow direction. In one variant, first air valve (e.g., intake valve) includes diaphragm, for instance, with one or more venting or flapping structures which, for example, open and close in response to a user's breath flow. In one embodiment, first air valve incorporated with several venting structures, e.g., louvers, moveable venting elements or structures. In one embodiment, first air back stop disposed proximal a direction of air flow of replaceable filter cooperates with first air valve to prevent air flow when first air value occupies a closed position. During exhale, user's breath through the chamber at least partially closes first air valve and opens at least partially second air valve (and in one embodiment an exhaust valve) to release exhaled air into the environment; thereby, this exhaust system prevents condensation build-up in air filtration device.

In one embodiment, air filtration system includes replaceable and interchangeable components, e.g., diaphragms or air flow back stops, to provide for customization, for instance, a pressure at which user's breath flow opens, closes, or partially opens or closes first or second air valve. In this way, air filtration device's interchangeable nature provide amenability to custom tailor environmental pressures or temperatures, body types, body size, or type of sporting event. In yet another embodiment, exhale system may include two air valves positioned away from each other, e.g., substantially orthogonal, to air flow inhale direction of inhale of first air valve.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

DETAILED DESCRIPTION

Figure 1:
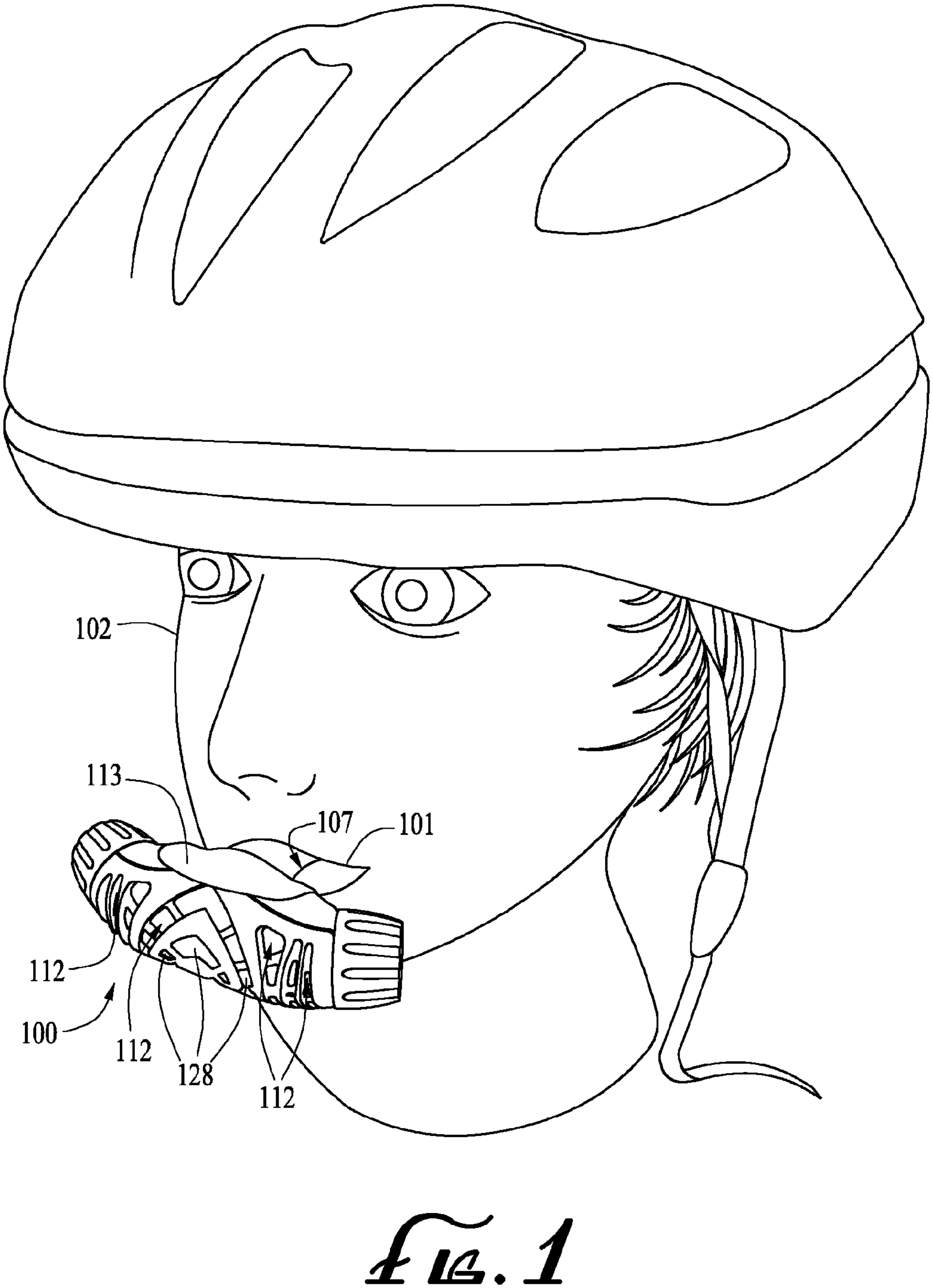
FIG. 1 is a front perspective view of air filtration apparatus in user's mouth in accordance with an embodiment of the present invention.

Reference is now made to the drawings wherein like numerals refer to like parts throughout.

Overview

In one salient aspect, the present invention discloses apparatus and methods for, inter alia, producing air filtration apparatus as well as provide custom capabilities, in one variant, to produce various configurations customized for a particular breathing style or type of environment to provide protection from, e.g., dust, pollen, rag weed, smoke, construction materials, glues, or the like. In particular, the present invention discloses apparatus and process to provide air filtration apparatus having separate input and output exhaust ports, for instance, to prevent condensation build-up while user exercising or breathing heavily into air filtration apparatus. Furthermore, the air filtration apparatus is easily assembled or disassembled and many of its components may be washed or replaced with minimal skill or effort. Furthermore, the present invention by effectively removing pollen and other allergens may reduce the frequency or dosage of or completely eliminate user's allergy medication requirements.

Furthermore, the present invention discloses air filtration apparatus applicable to protect user while participating in outdoor, high impact sports, e.g., motor cross racing, motor bicycle racing, all terrain vehicle riding, having adjustment and attachment capability, for instance, quick release fasteners to removably attach a multitude of washable or replaceable components. In one embodiment, multitude of protective devices includes carbon filter, front or back grille, mouthpiece, intake air valve and diaphragm operatively connected thereto, backstop of diaphragm from intake air valve(s), output air valve(s), and one or more diaphragms attached thereto. Furthermore, air filtration apparatus includes minimal weight composite materials and is ergonomically designed to improve user comfort and prevent unnecessary restriction of movement of a user. In one embodiment, mouth piece is integrated with a nose piece (e.g., fold down unit) and mouth piece seal. In one embodiment, nose piece at least partially prevents air flow through user's nostrils. In one variant of this embodiment, nose piece may restrict air flow to nose area, e.g, below user's nostril region, and thereby advantageously provide increased air flow through mouthpiece. As recognized by one skilled in the art, principles of the present invention are applicable to other applications, e.g., lung injury rehabilitation and/or supplement existing allergen medical programs so as to reduce a dosage of allergy medication and to prevent sickness when used in a dusty environment or an recovery room, e.g., hospital emergency room, rehabilitation center, homeless shelter, animal rescue shelter, or the like.

Exemplary Extension Apparatus

Referring now to FIGS. 1-4, exemplary embodiments of the air filtration apparatus of the invention are described in detail. It will be appreciated that while described primarily in the context of an air filtration apparatus for sporting events, at least portions of the apparatus and methods described herein may be used in other applications, such as for example and without limitation applications including employees working in a dusty or smoke laden environment, e.g., firefighters, construction workers, indoor or outdoor painters, asbestos abatement workers, seasonal allergy suffering individuals and the like. A myriad other functions will be recognized by those of ordinary skill in the art given the present disclosure.

As best illustrated in FIGS. 1-4, operation of air filtration assembly 100 is disclosed. Air filtration assembly 100 (shown in mouth 101 of user 102) includes replaceable filter 103. In one embodiment, replaceable filter 103 may be an organic carbon-based filter to remove air borne allergens and contaminates. In yet another embodiment, replaceable filter 102 may be activated carbon filter to capture and trap biomaterial, biohazards, dust, allergens, or the like. In yet another embodiment, replaceable filter may be layered, porous material integrated with beneficial properties of various filter materials and provides a progressive filtering capability (e.g., to remove contaminants in stages) as compared to many conventional single stage filtering units.

Figure 2:
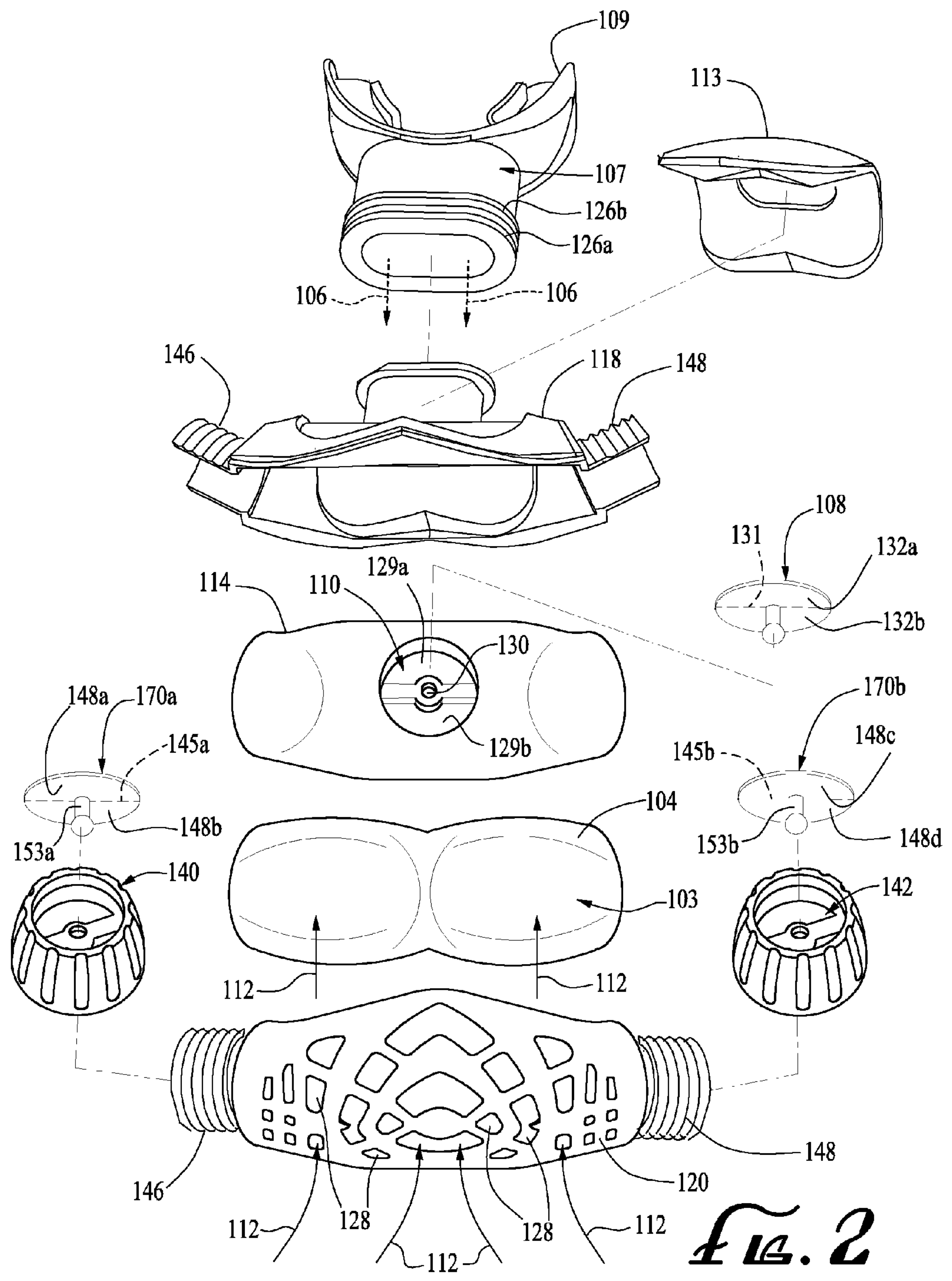
FIG. 2 is an exploded view of air filtration apparatus in accordance with an embodiment of the present invention.

As illustrated in FIG. 2, replaceable filter 103 may be a charcoal filter 104 (proximal to inner surface of front cover) and cotton filter 105 (as second stage filter) after charcoal filter 104. In contrast to conventional filtration systems having one type/size filter fits all approach, the present embodiment provides for replaceable filter 103 properties to be custom tuned or selected to eliminate or reduce a chosen user allergen particulate matter, e.g., smoke, dust, rag wed pollen, that may be inherent to a particular environment, e.g., mountain bicycling, jogging, running, walking, and roller blading in a smog laden valley or mountain range. In one embodiment, shape of replaceable filter 103 that dimensionality conforms to that of front cover 120 and back cover 118.

Figure 4:
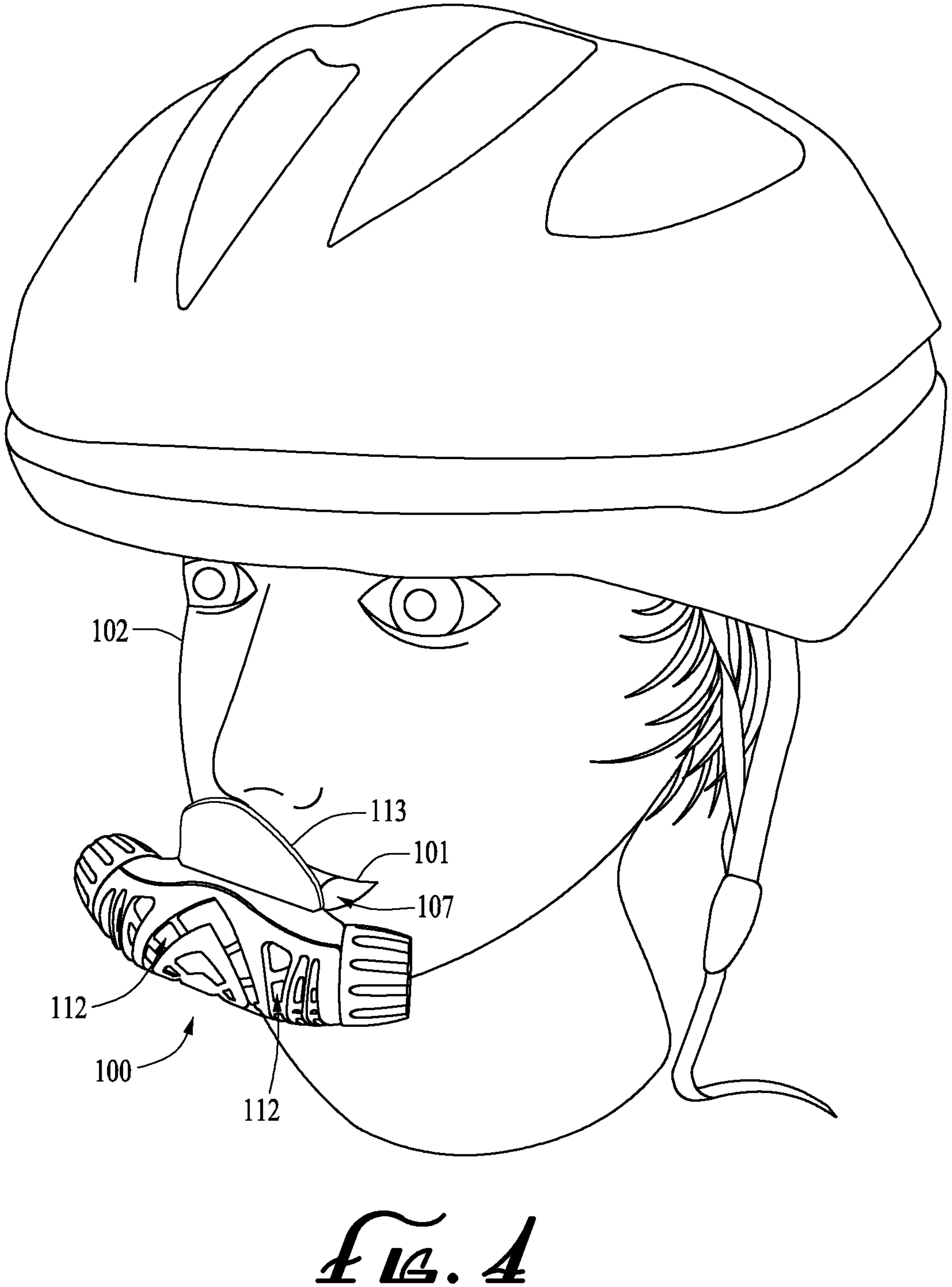
FIG. 4 is a front perspective view of air filtration apparatus in user's mouth using a nose piece in accordance with an embodiment of the present invention.

In one exemplary embodiment, mouth piece portion 107 fits into user's mouth 101 and, for example, snaps onto back cover 118 (shown in FIG. 2) using ridges 126*a*, 126*b*. In one variant, mouth piece 107 includes contoured plastic or rubber adapter 109 (shown in FIG. 2, 3) that inserts along an inner surface of user 102 mouth, e.g., occupying a circumferential area defined by user's tooth area 122. In another variant, mouth piece rubber adapter 109 fits over user's tongue 124. In yet another variant, mouth piece 107 includes one or more snap connection surfaces 126*a*, 126*b* that connects to snuggly removably snaps into back cover 118. In yet another embodiment, mouth seal and nose piece 113 folds up (e.g., retracted upward) to cover a lower nose portion, as shown in FIG. 4, of user 102. In another embodiment as illustrated in FIG. 1, mouth piece and nose piece 113 folds down (e.g., retracted downward) to lie on top surface of air filtration apparatus 100. In one embodiment, rubber adapter 109 advantageously allows user 102 to bite down while using apparatus 100, for instance, to prevent grinding of, for instance, user's tooth area 122. In one variant of this embodiment, nose piece 113 may restrict air flow to nose area, e.g., below user 102 nostril region, and thereby advantageously provide increased air flow through mouth piece 107.

In a first embodiment, user 102 inhales air flow 112 through mouth piece 107 using mouth 101. Suction force created by user 102 (e.g., when inhaling) causes air flow 112 that opens diaphragm 108 operatively connected at connection point 130 to intake air valve 110. In one embodiment, suction force causes diaphragm 108, e.g., flappers 132*a*, 132*b*, to flex along contour line 131, to open and allow air flow through openings 129*a*, 129*b* in backstop 114 for air flow 112 passing through openings 128 in front cover 120. While passing through openings 128, air flow 112, e.g., from a user's environment, passes through replaceable filter 103 and through chamber 116 bounded by front cover 120 and back cover 118 to mouth 101.

In one embodiment, air intake valve 110 and diaphragm 108 may be any combination of flapper, rubber stopper or disk device, differential pressure valve, or the like, that operatively connects with a structural component, e.g., such as contoured backstop 114, to limit range of motion, to assist in providing at least a partial air seal for diaphragm 108. In yet another variant, air intake valve 110 may be operatively connected with a diaphragm having multitude of venting or flapping structures, which, for instance, open and close position in response to user's breath flow and seal about, for instance, contoured backstop. In another variant, contoured backstop 114 includes one or more semi circular structures, e.g., openings 129*a*, 129*b*, and diaphragm 108 pivotally connects to air intake valve 110 to open or close.

In yet another variant, intake air valve 110 is incorporated with several venting structures, e.g., louvers or moveable venting elements or structures, including movements like a retractable window shade or blind. In one embodiment, backstop 114 is disposed proximal a direction of air flow (e.g., parallel to that of air flow surfaces) of replaceable filter 103 and cooperates with air intake valve 110 to prevent air flow out backcover 118 when the first air value 110 occupies closed position (e.g., flappers 132*a*, 132*b* flexed to closed position).

In another embodiment, user 102 exhales breath 106 through mouth piece 109 to close air intake valve 110 (closes 132*a*, 132*b*) and opens first exhaust air valve 140 (and in one embodiment both first exhaust air valve 140 and second exhaust air valve 142) to expel air 154*a*, 154*b* into the environment. In one exemplary embodiment, diaphragms, 170*a*, 170*b* open and close, e.g., flappers 148*a*, 148*b* open or close, e.g., along flex lines 145*a*, 145*b*, about connections 153*a*, 153*b* to first and second exhaust valves 140, 142, to expel air 154*a*, 154*b*. In one embodiment, first and second exhaust valves 140, 142 detachably connects along surfaces 146, 148 (e.g., screws into, snaps into, a combination thereof, or the like) to, for instance, ends of back cover 118 and front cover 120.

Advantageously, this present invention (as compared to conventional filtration apparatus having the same port for both input/exhaust breath) has separate exhaust air valve(s) 140, 142 and intake air valve 110 to reduce or prevent condensation or build-up of water vapor exhaled with user's breath. In one embodiment, the valve(s) 140, 142 are pointed toward the ground so that condensation will fall to the ground instead of building up side the apparatus 100. In one embodiment, separate exhaust and intake valves prevent air filtration apparatus condensation when there is temperature differential between environment and user's breath, e.g., environment has a temperature about 50 degrees and user's breath is about 110 degrees while perspiring. In another embodiment, as compared to conventional air filtration systems, replaceable filter 103 is positioned after backstop 118 and not accessible by a user's breath during exhale stage. For instance, when air intake valve 110 is closed, replaceable filter 103 avoids hot air, e.g., moist air or hot vapor, expelled by user 102 breathing heavily (e.g., perspiring or during exercise) while at least one of the exhaust air valves 140, 142 is open.

In yet embodiment, air filtration apparatus 100 includes, advantageously as compared to conventional straight walled non-contoured devices, angled walls 160, 162 (e.g., wrap-around contoured chamber) formed by front cover 120 and back cover 118. As compared to conventional non-contoured air filtration devices, angled walls 160, 162, increases air flow and suction between mouth piece 107 and either intake valve 110 or exhaust valve(s) 140, 142 when in, for instance, in an open position. In one alternative embodiment, angled walls 160, 162 may be chosen between an angle of 25 degrees to 45 degrees (e.g., to a direction of exhaust valves 140, 142) so as to maximize air suction/unit of user breath for air chamber formed by enclosed surfaces substantially surrounded by front cover 120 and back cover 118. In one embodiment, front cover 120 and back cover 118 snap together (and, in one alternative embodiment, may be attached solely by snapping means or in combination with an epoxy adhesive to further secure each to one another).

In one alternative, air filtration system 100 includes replaceable and interchangeable components, e.g., diaphragms or air flow back stops, to allow customization, for instance, of a pressure at which user's breath flow opens, closes, or partially opens or closes air valve(s), e.g., intake air valve 110, exhaust air valve(s) 140, 142. In this way, air filtration device 100 interchangeable parts may be custom tailored to environmental pressures or temperatures, body types, body size, or type of sporting event. In one embodiment, exhale system may include two air valves positioned orthogonal to a direction of inhale air flow from that of an inhale air valve to minimize condensation, for instance, water vapor formed when a user's breath temperature inside chamber has a different, for example a 10 to 50 degree temperature differential, than that of the environment outside the chamber.

Advantageously as shown in one embodiment as compared to conventional single intake/exhaust openings, the air filtration device by positioning, e.g., in one embodiment, substantially orthogonal to one another, so that separate, individually actuated, air intake and exhaust valves provides a system for separating exhale and inhale breathing stages. For instance, the device design provides inherent separation properties of air intake (a removable filter at least partially shielded when air intake valve is closed) from that of exhaust intake (when valve is open) to prevent condensation from hot air exhaling entering removable filter. Furthermore, because each intake and exhaust is separated, each system can be designed substantially independently for maximize performance as well as customize intake and exhaust properties individually/separate for an individual. Advantageous as compared to conventional fixed apparatus designs, the present invention having, in one embodiment, snap together or screw-on construction provides for easy interchanging and washing of components (after use). In addition, in contrast to conventional systems, the present contoured design (angled design) provides stream lined as well as better channel or vessel for intake as well as exhale of air exchanges.

Exemplary Methods

Figure 5:
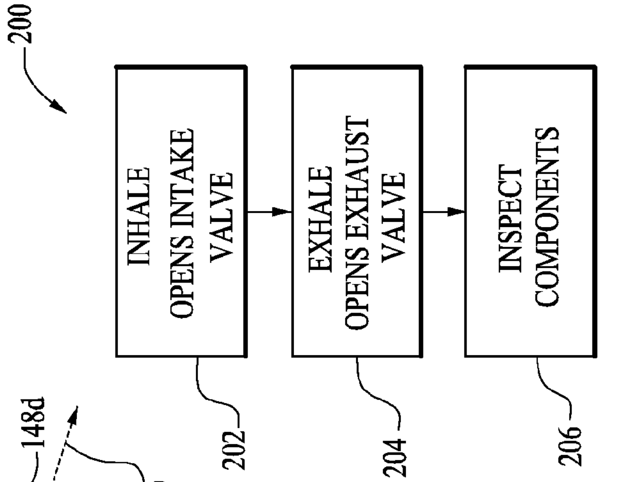
FIG. 5 is a logical flow diagram illustrating one exemplary embodiment of a method of operation of air filtration apparatus in accordance with an embodiment of the present invention.
Figure 3:
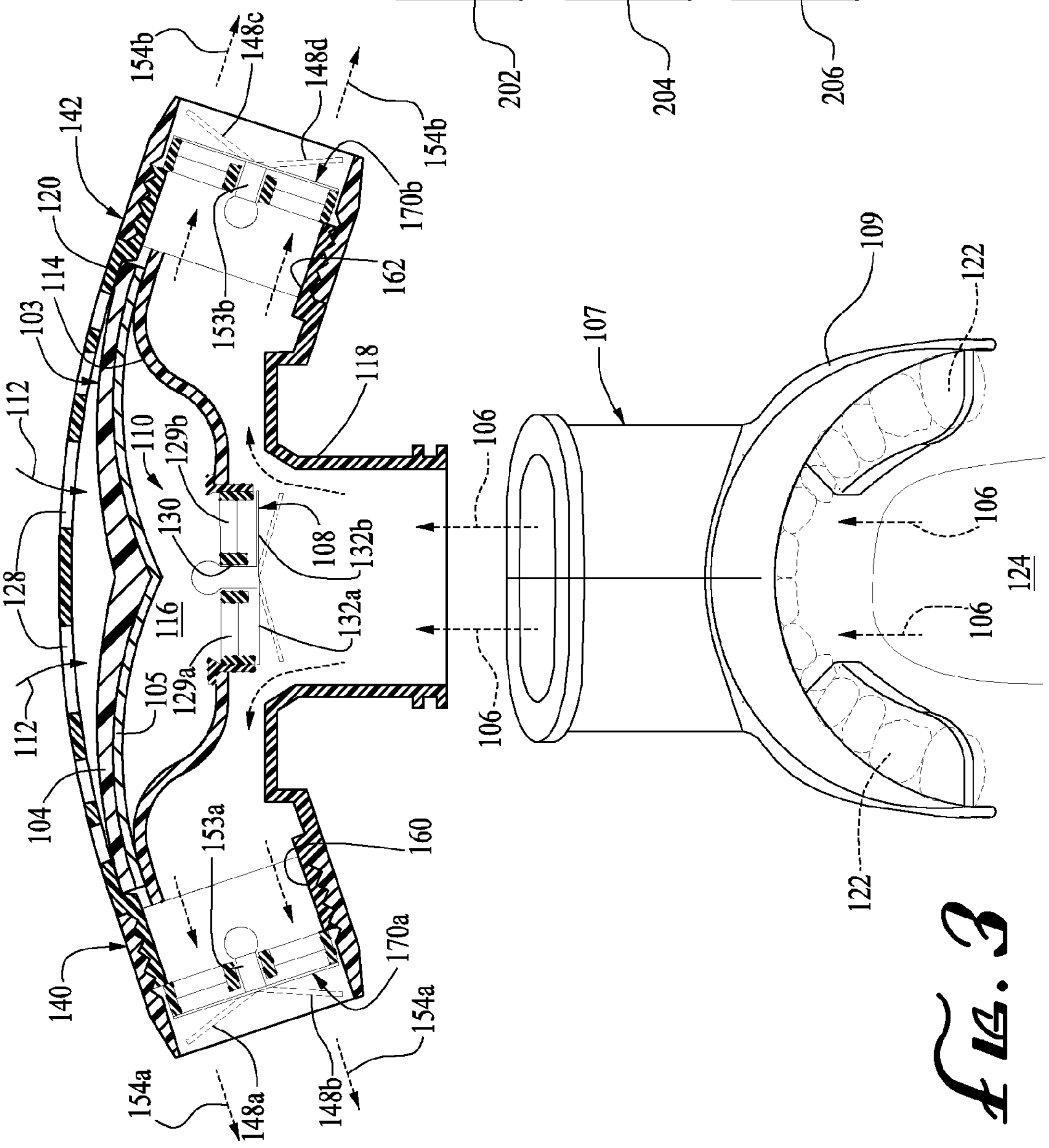
FIG. 3 is a top-cut away view of air filtration apparatus of intake valve in open and closed positions, exhaust valves and movable diaphragm in open and closed positions, and mouth piece with insertion between user's teeth and tongue in accordance with an embodiment of the present invention.

Referring now to FIG. 5, an exemplary embodiment of a method 200 for manufacturing using the aforementioned air filtration apparatus is described. While described primarily in the context of the exemplary embodiments of apparatus 100 shown in FIGS. 1-5, it will be appreciated that the methodology presented herein may be readily adapted to many different configurations of apparatus 100 as recognized by those of ordinary skill in the art.

In step 202, user 102 creates suction force using mouth 101 to cause incoming airflow 112 (e.g., air from environment), which opens diaphragm 108 and causes airflow 112 through chamber within air filtration apparatus 100 to user's mouth 101. In step 204, user 102 exhales through mouth 101 to close diaphragm 108 and to open diaphragms 170*a*, 170*b* to exhale air 154*a*,154*b* through valves 140, 142. In step 206, user 102 quick snap disassembles air filtration apparatus 100 to clean and wash components including replaceable filter 103. In one variant, properties of replaceable filter 103 chosen to meet environmental requirements of a user, e.g., smoke or smog laden valley, where user 102 wishes to use air filtration apparatus 100.

It will be appreciated that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. An air filtration assembly comprises:

a front cover;

a back cover;

a mouth piece;

a first valve coupled to a first diaphragm to open and close in response to an inhale response of flow of a user's breath;

a second valve coupled to a second diaphragm to open and close in response to an exhale response of the flow of the user's breath; and a wrap-around contoured chamber formed by the front cover and the back cover having approximately 25 to 45 degree angled walls between the mouth piece in the direction of the second valve and configured to increase suction between the mouth piece and at least one of the first and the second valves.

2. The air filtration assembly of claim 1, further comprising a replaceable filter, the replaceable filter shaped to conform to an inner surface dimensionality of a backstop and to be substantially shielded from the exhale response of the user's breath by a closed position of the first valve.

3. The air filtration assembly of claim 1, wherein the first valve and the second valve are positioned substantially orthogonal to one another to increase effective isolation properties between inhale and exhale stages.

4. The air filtration assembly of claim 1, further comprising a third valve positioned substantially oppositely directed and in a same plane as the second valve, the third valve coupled to a third diaphragm to open and close in response to the exhale response of the flow of the user's breath.

5. The air filtration assembly of claim 2, wherein the backstop is operatively connected to the first diaphragm to provide a restriction of motion of the first diaphragm and the replaceable air filter in operation when either in an open or a closed position as well as provide isolation of the inhale response and the exhale response of the flow of the user's breath.

6. The air filtration assembly of claim 1, further comprising a mouth piece seal and a nose piece that retractably extends to cover a user's nose; wherein the second valve comprises a diaphragm have a folding venting or flapping structure to open and close in response to the flow of the user's breath.

7. An air filtration assembly comprises:

a mouth piece;

a front cover;

a back cover;

a replaceable filter;

a first valve operatively coupled to a first flapper to at least partially open in response to an inhale response of a user to allow air to enter the replaceable filter and to at least partially close in response to an exhale response of a user and to at least partially shield the replaceable filter during the exhale response;

a second and third valve operatively disposed orthogonally to the first valve and operatively coupled to a second and third flapper valves respectively to at least partially open in response to an exhale response of a user to exhaust air from the user; and a wrap-around contoured chamber formed by the front and the back cover having approximately 25 to 45 degree angled walls between the mouth piece in the direction of the second and the third flapper valves, the approximately 25 to 45 degree angled walls configured to increase suction between the mouth piece and at least one of the first, second and third flapper valves.

8. The air filtration assembly of claim 7, further comprising a replaceable filter, the replaceable filter shaped to conform to a contour shape of a backstop and to be substantially shielded from the exhale response of the user through a closed position of the first valve.

9. The air filtration assembly of claim 7, wherein the second valve and the third valve are positioned substantially oppositely directed and in a same plane as one another.

10. The air filtration assembly of claim 7, wherein the backstop operatively connected to the first diaphragm to provide a restriction of motion of the first diaphragm when either in an open or a closed position as well as provide isolation of the inhale response and the exhale response of the user.

11. The air filtration assembly of claim 7, further comprising a mouth piece seal and a nose piece that retractably extends to cover a user's nose; wherein the second valve and the third value operatively connect to a diaphragm have a folding venting or flapping structure to open and close in response to the exhale and inhale response of the user.

12. The air filtration assembly of claim 7, further comprising a mouth piece seal and a nose piece that retractably extends to cover a user's nose; wherein the second valve and the third value operatively connect to a diaphragm have a folding venting or flapping structure to open and close in response to the exhale and inhale response of the user; wherein the second valve and the third valve are positioned downward to provide escape of condensation during the exhale response in a downward direction relative to a resting positional direction of the air filtration assembly.

* * * * *